United States Patent [19]

Frankel et al.

[11] Patent Number: 5,240,834
[45] Date of Patent: Aug. 31, 1993

[54] SOLUBILIZATION OF PROTEIN AFTER BACTERIAL EXPRESSION USING SARKOSYL

[75] Inventors: Stewart A. Frankel, Brooklyn; Leslie A. Leinwand, Pelham, both of N.Y.

[73] Assignee: Albert Einstein College of Medicine of Yeshiva University, Bronx, N.Y.

[21] Appl. No.: 644,089

[22] Filed: Jan. 22, 1991

[51] Int. Cl.$^5$ .......................... C12P 21/00; C12N 9/88
[52] U.S. Cl. .................................. 435/71.2; 435/71.1; 435/232; 435/259; 530/412; 530/825
[58] Field of Search ...................... 435/71.1, 71.2, 232, 435/259; 530/412, 825

[56] References Cited

U.S. PATENT DOCUMENTS 5,082,775  1/1992  McCaman et al. ................. 530/412

OTHER PUBLICATIONS

Darby, Nigel J., and Creighton, Thomas E., "Folding Proteins", Nature, vol. 344, Apr. 19, 1990, pp. 715–716.
Schein, Catherine H., "Production of Soluble Recombinant Proteins in Bacteria", Bio/Technology, vol. 7, Nov. 1989, pp. 1141–1149.
Mitraki, Anna and King, Jonathan, "Protein Folding Intermediates and Inclusion Body Formation", Bio/Technology, vol. 7, Jul., 1989, pp. 690–697.
Heeke, Gino Van, and Schuster, Sheldon M., "Expression of Human Asparagine Synthetase in Escherichia coli", The Journal of Biological Chemistry, vol. 264, No. 10, Apr. 5, 1989, pp. 5503–5509.
Leinwand, Leslie A. et al., "Bacterial Expression of Eukaryotic Contractile Proteins", Cell Motility and the Cytoskeleton, 14:3–11, (1989), pp. 3–11.
Hoess, Adolf et al., "Recovery of Soluble, Biologically Active Recombinant Proteins from Total Bacterial Lysates Using Ion Exchange Resin", Bio/Techology, vol. 6, Oct., 1988, pp. 1214–1217.
Frankel, Stewart, "Expression of Dictyostelium Actin in E. coli", The Einstein Quarterly, vol. 6, No. 3, Summer, 1988 p. 152.
Schein, Catherine H., and Noteborn, Mathieu H. M., "Formation of Soluble Recombinant Proteins in Escherichia coli is Favored by Lower Growth Temperature", Bio/Technology, vol. 6, Mar., 1988, pp. 291–294.
Hartley, D. L., and Kane, J. F., "Recovery and Reactivation of Recombinant Proteins", Biochemical Society Transactions, vol. 16, (1988), pp. 101–115.
Frankel, et al., "Expression of Dictyostelium Actin in E. coli", Journal of Cell Biology, vol. 103, (1986), p. 1159.
Watt et al., "Expression and Characterization of the Human c-myc DNA-Binding Protein", Molecular and Cellular Biology, vol. 5, No. 3, Mar., 1985, pp. 448–456.
Ferguson et al., "Isolation and Analysis of an Abelson Murine Leukemia Virus-encoded Tyrosine-specific Kinase Produced in Escherichia coli", The Journal of Biological Chemistry, vol. 260, No. 6, Mar. 25, 1985, pp. 3652–3657.
Marston, Fiona A. O., "The Purification of Eukaryotic Polypeptides Synthesized in Escherichia coli", Biochem. J., vol. 240, (1986), pp. 1–12.

Primary Examiner—Herbert J. Lilling
Attorney, Agent, or Firm—Amster, Rothstein & Ebenstein

[57] ABSTRACT

This invention relates to two methods for solubilizing proteins which are rendered insoluble by bacterial expression. One method comprises directly lysing the host bacterial cells with the detergent Sarkosyl. The other method comprises conventional lysing of the bacteria followed by an extraction process using Sarkosyl and fractionation. These methods render the proteins soluble. They do not entail harsh denaturation of the proteins, and therefore do not require renaturation of the proteins in many cases. Rather, they render the proteins soluble, in their native form.

16 Claims, 5 Drawing Sheets

SOLUBILIZATION OF PROTEIN AFTER BACTERIAL EXPRESSION USING SARKOSYL

FIELD OF THE INVENTION

This invention relates to two methods for solubilizing bacterially expressed proteins which are rendered insoluble by the bacterial expression process. These methods utilize the detergent Sarkosyl (N lauryl sarcosine or any other detergent which is an N amide derivative of sarcosinate). One method is a direct lysis of host bacterial cells in the presence of Sarkosyl detergent. The other method is an extraction process performed on insoluble protein, also requiring Sarkosyl detergent.

During purification of bacterially expressed proteins, proteins may become insoluble due to a variety of mechanisms. One mechanism which renders proteins insoluble is co-aggregation of the proteins with bacterial outer membrane components, such as outer membrane proteins and lipopolysaccharides. Once the proteins become insoluble, strong denaturants are necessary for resolubilization. The methods of this invention allow for the solubilization of bacterially-expressed proteins which are rendered insoluble by the bacterial expression process without resorting to strong denaturants, such that functional protein may be recovered and purified. In particular, the methods of this invention allow for the efficient separation of solubilized bacterially-expressed proteins from contaminating outer membrane components, with subsequent removal of the detergent.

BACKGROUND OF THE INVENTION

Bacterial expression systems have been utilized to produce large quantities of homogeneous proteins whose function may then be assayed and studied irrespective of the sequence of that protein or its abundance in its natural host. However, the bacterial expression process renders many proteins insoluble. Once a protein is rendered insoluble, the protein must be solubilized.

Certain methods have been developed to solubilize proteins which have been rendered insoluble by bacterial expression. However, the solubilization methods created heretofore necessarily entail denaturation of the protein. As a result, the protein must necessarily be renatured. This renaturation process may be costly and time consuming. In many instances, renaturation is not possible. Therefore, a need has arisen to create a method for solubilizing bacterially-expressed proteins which does not denature the proteins, and therefore eliminates the necessity to renature altogether.

SUMMARY OF THE INVENTION

This invention relates to two methods for solubilizing bacterially-expressed proteins, wherein the proteins are not denatured, but rather may be separated from contaminating bacterial outer membrane components while remaining in their native form. These nondenatured proteins may then be assayed for their function and purified without the necessity of renaturing the proteins prior to purifying and assaying the proteins.

The proteins to be studied are first expressed in bacterial systems, which requires inserting the coding sequence for a protein in an appropriate plasmid expression vector. During the lysis of the bacteria, the proteins are rendered insoluble. The first method of this invention comprises solubilizing-bacterially expressed proteins by directly lysing the bacteria with the detergent Sarkosyl. The second method comprises conventional lysing methods (such as the French press method, sonication, or lysozyme digestion followed by freezing and thawing) followed by the extraction of insoluble protein with Sarkosyl and EDTA, followed by fractionation.

Figure 2:
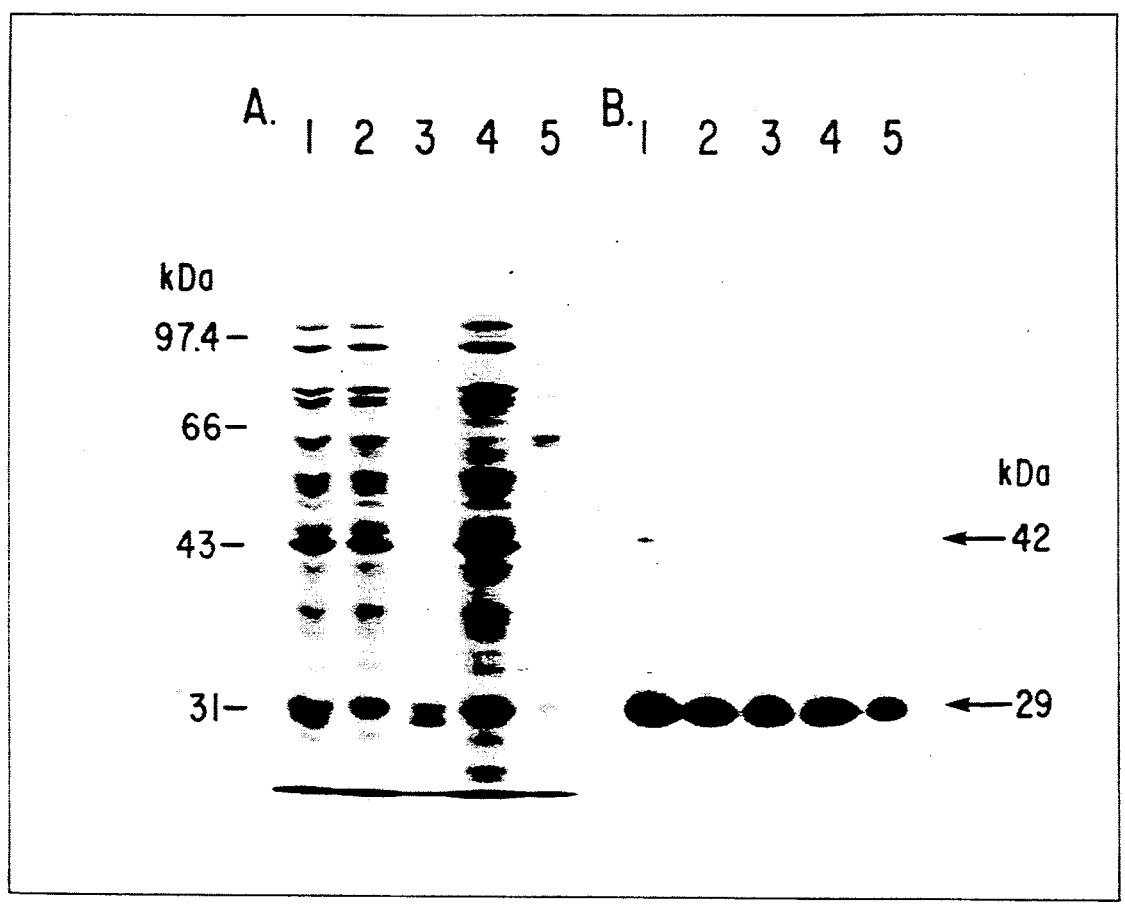
FIG. 2 represents the fractionation of both full-length and truncated actin after Sarkosyl lysis. As in FIG. 1, each fraction has been subjected to SDS polyacrylamide electrophoresis and protein has been visualized either by Coomassie stain or immunoblot.

Table I represents the quantitation of data illustrated in FIG. 2. Substantial amounts of both 29-kDa and 42-kDa actin remain soluble after direct Sarkosyl lysis.

Figure 3:
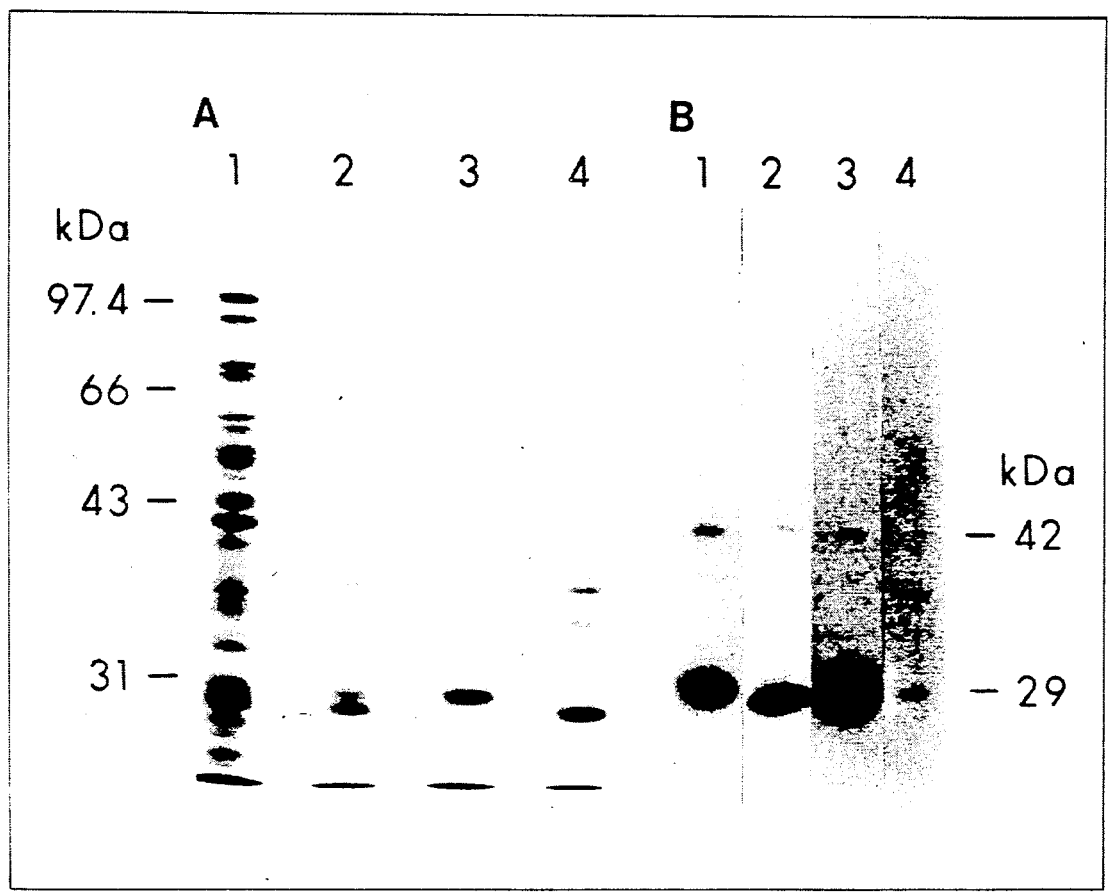

FIG. 3 represents the fractionation of both 29-kDa and 42-kDa actin after French press lysis and Sarkosyl extraction. As in FIG. 1, fractions were analyzed by SDS electrophoresis and visualized either by Coomassie-stained gel or immunoblot.

Table II represents the ability of 29 kDa actin to bind DNase I, in comparison to the ability of *Dictyostelium discoideum* (D.d.) actin to bind DNase I, as measured by affinity chromatography.

Figure 4:
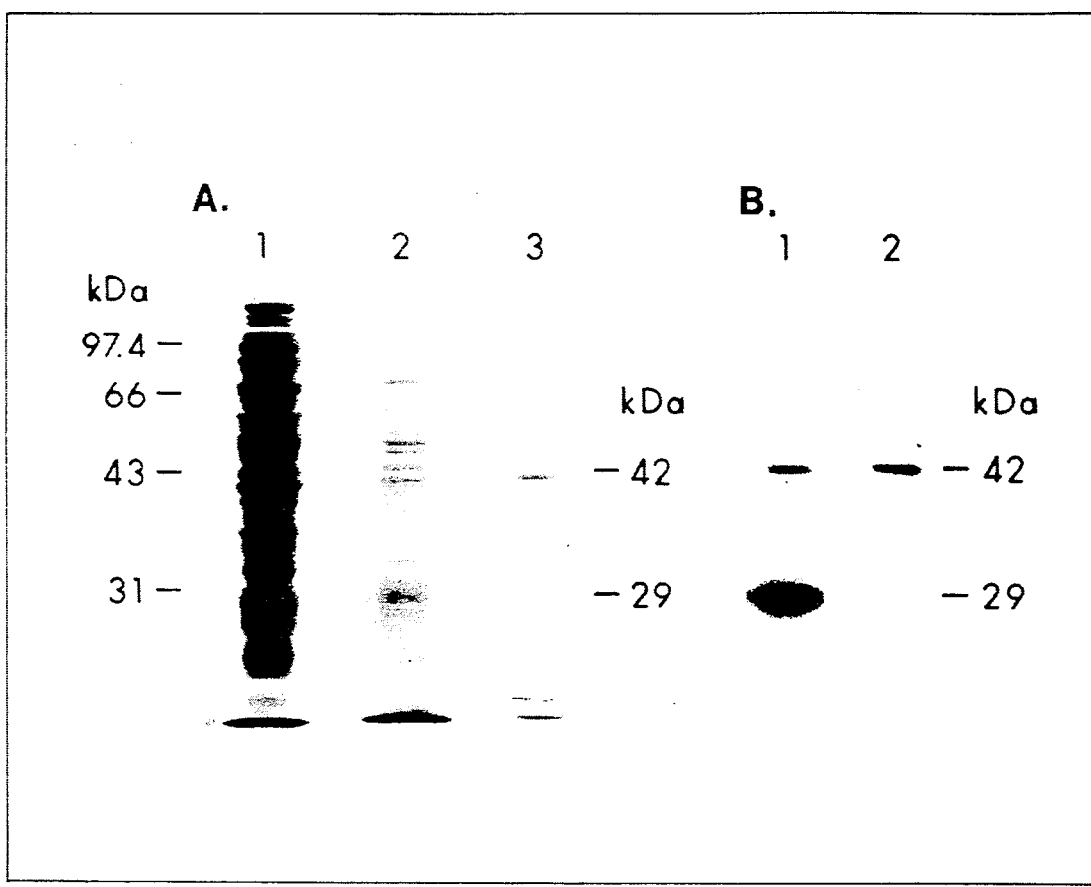

FIG. 4 represents the purification of 42-kDa actin using DNase I affinity chromatography and gel filtration in 0.8M NaCl. Panel A is a Coomassie-stained gel at three stages in the purification. Panel B is an immunoblot of fractions from the gel filtration column.

Figure 5:
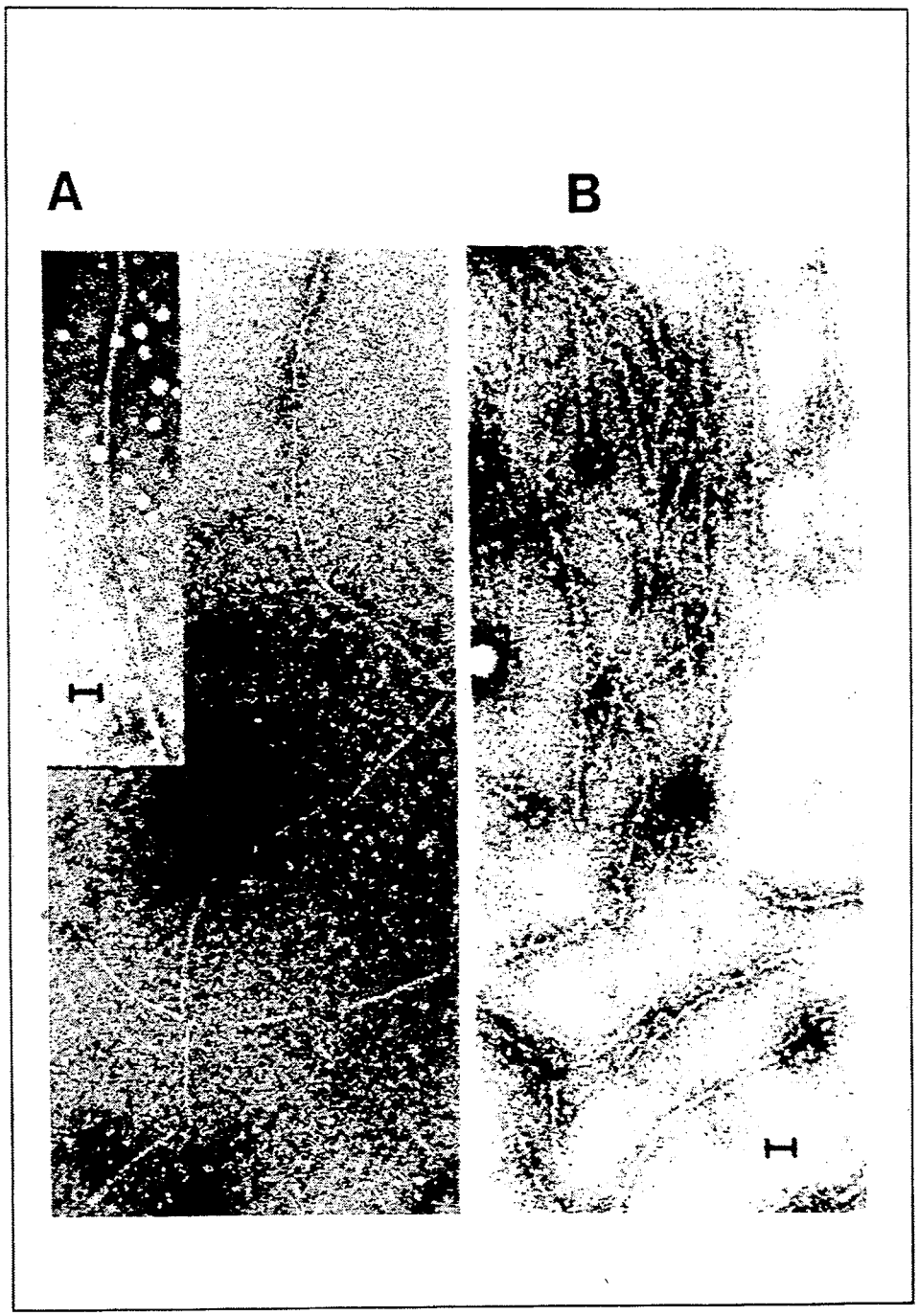

FIG. 5 represents the ability of purified 42-kDa actin to form filaments, and the ability of 42-kDa actin filaments to bind a form of myosin (myosin sub fragment-1) in an ATP-sensitive manner. Both properties are characteristic of native actin. Actin is one protein which cannot be renatured after denaturation.

DETAILED DESCRIPTION OF THE INVENTION

Bacterial expression is a versatile process which allows for the production of any protein for commercial or research purposes. However, a problem which arises with some proteins during bacterial expression is that the proteins can only be extracted in an insoluble form. Furthermore, strong denaturants have heretofore been necessary for their subsequent solubilization. This invention allows for the solubilization of insoluble proteins after bacterial expression. The methods of this invention, in contrast with other methods of solubilizing proteins, do not require denaturation and subsequent renaturation of the protein. This is a particular advantage for the classes of protein which cannot be renatured. The methods of this invention therefore allow for commercial use of bacterial expression for many proteins heretofore not suitable for bacterial expression because it yields soluble, nondenatured protein.

This invention comprises two procedures for lysing the bacteria and fractionating the lysates, consisting of: (1) lysing the bacteria by a light lysozyme digestion followed by the addition of Sarkosyl detergent, and several obligate steps of fractionation following lysis, and (2) lysing the bacteria by other standard methods, collecting the insoluble protein and extracting this insoluble protein with Sarkosyl detergent and EDTA, followed by fractionation.

A protein which may be solubilized after bacterial expression by the methods of this invention is actin in either its full-length (42-kDa) form or in a truncated (29-kDa) mutant form. Actin is normally a soluble protein. Its insolubility after bacterial expression and lysis may be due to co-aggregation of the actin with bacterial outer membranes during bacterial lysis. This method can also be used on other proteins, including *Dictyostelium discoideum* myosin light chain kinase. Sarkosyl detergent is a relatively mild chaotrope with a specific effect upon this co aggregation process since it does not solubilize the bacterial outer membrane. The Sarkosyl lysing method of this invention produces soluble actin after bacterial expression.

EXAMPLE 1

Solubilization of Bacterially-Expressed Actin by Direct Sarkosyl Lysis

Culture Growth

Plasmid expression vectors were constructed as described in Frankel et al., "Expression of Actin in *Escherichia Coli*", *Journal of Biological Chemistry*, Vol. 265, No. 29, Oct. 15, 1990. For expression of actin in large-scale culture, a 1/100 dilution of an overnight culture was inoculated into 1 liter of M10+medium (60 mM $Na_2HPO_4$, 11 mM $K_2PO_4$, 37 mM $NH_4Cl$, 9.0 mM NaCl, 1.0 mM $MgSO_4$, 0.05 mM $CaCl_2$, 0.05 mM $MnCl_2$, 0.03 mM $FeCl_3$, 0.5% casamino acids, 1% glycerol, 5% LB broth, made with autoclaved distilled $H_2O$ followed by filter sterilization) plus 40 ug/ml ampicillin, incubated at 37° C. in a 2 liter baffled flask with vigorous shaking, grown to an $OD_{550}$ of 0.2–0.3 and then induced with 4 mM IPTG. When the cells reached an $OD_{550}$ of 0.95, the flasks were chilled in an ice-water bath for 20–30 min. Enriched minimal medium is used because growth in strict minimal medium is very slow. After the cultures were grown, Sarkosyl lysis was performed.

Direct Sarkosyl Lysis

All procedures were at 4° C. or on ice. Bacteria from one liter of culture grown to an absorbance at 550 nm of 0.95 were sedimented and washed with a buffer containing 20 mM Tris, pH 8 at 4° C., and 50 mM NaCl. Washed cells were resuspended in 15 mls of STE (10% sucrose, 100 mM Tris, pH 8 at 4° C. 1.5 mM EDTA), and lysozyme was added to 100 μg/ml to perform a light digestion. Lysozyme digestion may be facilitated by a buffer containing EDTA, sucrose and Tris (pH 8.0). The cells were incubated on ice 10–15 min. or until lysis competent. Lysis competence may be assessed by resuspending a small volume of bacterial suspension into a 200 fold excess of distilled water (hypotonic solution). The cells were then added to 132 mls of divalent cation free dilution solution with a pH of 8.0, which is capable of maintaining the tonic balance of the bacteria and the stability of the expressed protein. This dilution solution may comprise 50 mM NaCl, 15 mM buffer at pH 8.0, 0.5–5 mM dithiothreitol, and protease inhibitors. After dilution, the volume may be between 5 and 15 times the volume of the cell suspension during lysozyme digestion. To lyse the bacteria, while stirring, 3 mls of 10% Sarkosyl was added to a 0.2% final concentration. For lysis, the Sarkosyl may be added to a final concentration of 0.2–2%. While adding Sarkosyl, the rate of stirring was increased to compensate for the increased viscosity, but turbulence was avoided. After the addition of Sarkosyl, the lysate contained: 15 mM triethanolamine (pH 8 at 4° C.), 50 mM NaCl, 2.5 mM ATP, 1.0 mM GDP, 1.0 mM DTT, 20 ug/ml aprotinin, 10 ug/ml leupeptin, 5 ug/ml pepstatin, 2.5 ug/ml chymostatin, 0.43 mM PMSF, 0.43 mM o-phenanthroline, 10 mM Tris, 0.16 mM EDTA, 1.0% sucrose (the last three were from STE). GDP was included to maintain EF Tu in a native state. After 2 min., the lysate was mildly sonicated to reduce viscosity due to high molecular weight nucleic acid: seven 10 second bursts at 90 watts (Heat Systems-Ultrasonics, setting 2). The lysate was then centrifuged at 32,000×g for 11 min. so as to separate bulk soluble protein from insoluble material. The supernatant was collected and the Sarkosyl was sequestered by adding octylglucoside to a concentration of 2%, using a 25% stock. After stirring the supernatant for 5 min., $MgCl_2$ and $CaCl_2$ were added to concentrations of 1.25 mM and 1.06 mM respectively. The estimated free concentration of each divalent cation was 0.1 mM. After stirring for 20 min. this fraction was centrifuged at 60,000×g for 12 h to pellet 30 S ribosome subunits.

In general, Sarkosyl may be sequestered by adding nonionic detergent in at least a 5-fold weight excess over the Sarkosyl detergent. This nonionic detergent may be octylglucoside. Sarkosyl sequestration may be followed by the addition of divalent cations to stabilize the protein.

Sequestration may also be followed by one of three methods to remove all detergent. One method, applicable to sequestration using any nonionic detergent, involves binding the protein to a solid resin matrix and washing all of the detergent out of the resin matrix. A second method, applicable only to sequestration using octylglucoside, involves dialysis in which the dialysis membrane has a molecular weight cut-off of at least 30,000 daltons. A third method, applicable only to sequestration using octylglucoside, involves concentration of the sample using a 30,000 dalton cut off membrane followed by dilution of the concentrated sample into a detergent-free solution. Another method of removing detergent does not require sequestration. This alternative method involves precipitation of Sarkosyl by adding a several millimolar excess of divalent cation over EDTA and removing the Sarkosyl by centrifugation.

RESULTS

1 Actin Is Soluble After Direct Sarkosyl Lysis

Figure 1:
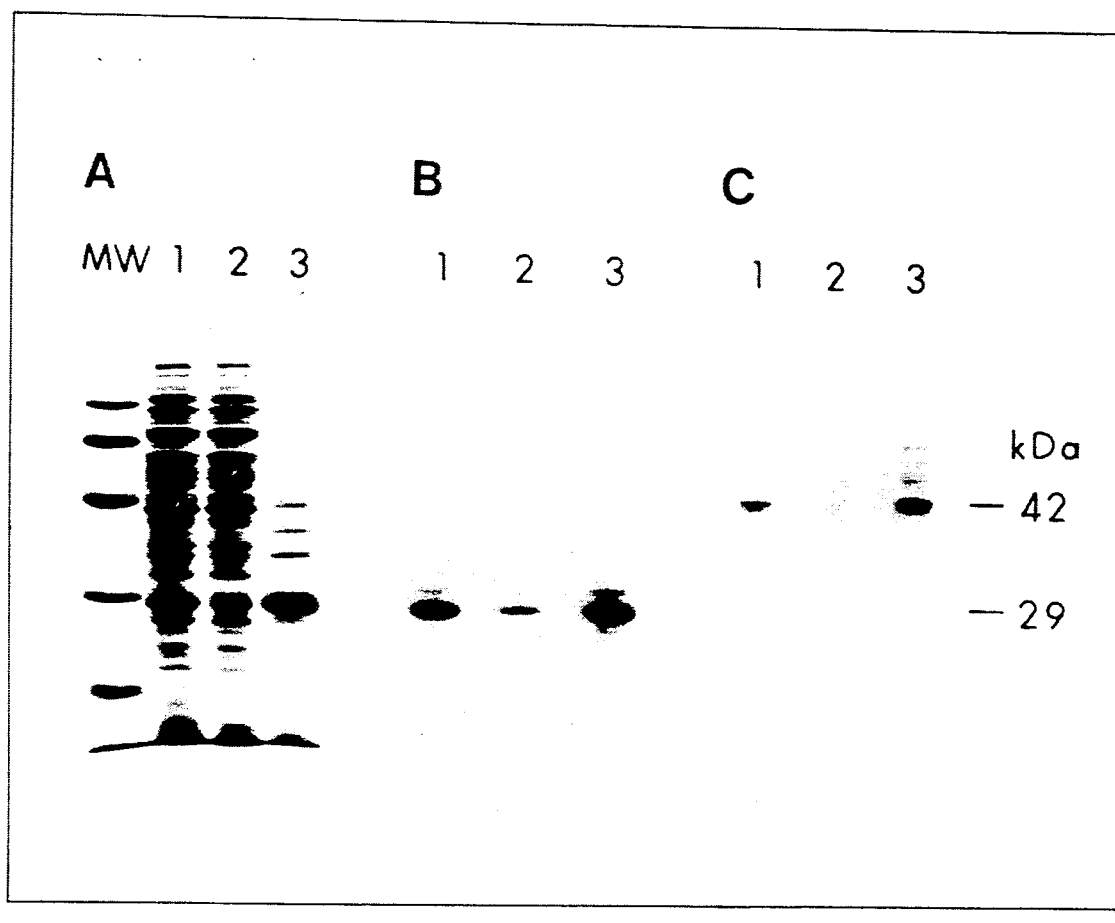
FIG. 1 represents fractionation of both 29-kDa (truncated) and 42-kDa (full length) actin without Sarkosyl lysis. Panel A is a Coomassie stained gel, after SDS polyacrylamide electrophoresis. Panel B shows an immunoblot of the samples in Panel A, from the region of the immunoblot containing 29-kDa actin. Panel C shows the same immunoblot, from the region containing 42-kDa actin.

After French press lysis, bacterially expressed actin is insoluble. FIG. 1 represents fractionation of both 29-kDa actin and 42-kDa actin after French press lysis. The fractions were analyzed by immunoblots, and the immunoblots were quantitated by densitometry. However, soluble full length 42-kDa actin and soluble truncated 29-kDa actin were recovered after direct Sarkosyl lysis. Lane 1 is a sample of total lysate; lane 2 is a sample of the supernatant after low speed centrifugation; lane 3 is a sample from the pellet after low speed centrifugation. The relative loadings of lanes 1 and 2 are equal, while 4 times more sample was loaded in lane 3.

The lane labelled MW contains molecular weight markers.

Table I shows fractionation of actin after Sarkosyl lysis. FIG. 2 represents a Coomassie stained gel and an immunoblot of the fractions listed in Table I. Panel A is a Coomassie stained gel and Panel B is an immunoblot of the same samples. Lane 1 is a sample of total lysate; lane 2 is a sample of the low speed supernatant; lane 3 is a sample from the low speed pellet; lane 4 is a sample of postribosomal supernatant; lane 5 is a sample from the ribosome pellet. Each lane is loaded so as to have roughly equal amounts of 29-kDa actin, as determined by Western analysis.

TABLE I
SOLUBILITY OF ACTIN AFTER SARKOSYL LYSIS AND OCTYLGLUCOSIDE SEQUESTRATION

|  | 29 kDa Actin |
| --- | --- |
| Total Lysate | 100% |
| Low Speed Supernatant | 59% |
| Low Speed Pellet (Outer Membrane) | 37% |
| Post-Ribosomal Supernatant | 19% |
| Ribosome Pellet | 18% |
|  | 42 kDa Actin |
| Total Lysate | 100% |
| Low Speed Supernatant | 93% |
| Low Speed Pellet (Outer Membrane) | 6% |
| Post-Ribosomal Supernatant | 55% |
| Ribosome Pellet | 17% |

Lysis and fractionation were performed. Yields were quantitated by the densitometric scanning of immunoblots. In adition, it was determined that the low and high speed supernatants contained approximately 160 and 75 mg of DNA, respectively. The high speed centrifugation was overnight; some loss of actin occurred at this step, probably due to proteolysis. While these numbers are from one experiment, comparable results have been obtained in repetitions of the experiment.

2. 42-kDa Actin Binds DNase I During Purification

A characteristic property of actin is the ability to bind DNase I. In the course of purifying 42-kDa actin, it was possible to demonstrate its ability to bind DNase I. The complete purification was performed as follows:

A low speed supernatant was obtained as described under "Sarkosyl lysis," octylglucoside and divalent cations were added, sodium azide was added to 0.02%, and the solution was batch absorbed to DNase I affinity resin for 2.5 hours. The resin was batch washed with 15 bed volumes of high salt buffer (25 mM triethanolamine, pH 8.0 at 4° C., 0.8M NaCl, 0.02% azide, 1.0 mM ATP, 1.0 mM GDP, 5.0 mM NaPP, 0.25 mM DTT, 0.1 mM EDTA, 1.38 mM McCl$_2$, 0.945 mM CaCl$_2$, 0.5 mM PMSF; the estimated free concentration of each divalent cation was 0.1 mM). The resin was then loaded into a column and washed with 5 bed volumes of high salt buffer. Most of the buffer above the bed was drained, and 100% deionized formamide equal to 30% of the bed volume was added, gently resuspending the resin and incubating for 10 min. The resin bed was completely drained, and residual liquid was removed by pushing air through the bed. 40% formamide disrupts the interaction of actin with DNase I, and allows actin to be eluted from the affinity resin. The eluate was diluted by the addition of high salt buffer, so that the formamide concentration was 30%. The eluate was clarified of resin fines, and immediately loaded onto a Sephadex G-150 column (1.5 × 68 cm) equilibrated in a modified high salt buffer (25 mM triethanolamine, 0.8M NaCl, 0.02% azide, 0.1 mM EDTA, 5 mM NaPP, 0.2 mM ATP, 0.5 mM DTT, 0.138 mM CaCl$_2$; free CA$^{++}$ was estimated at 5 uM). The column was run using the modified high salt buffer, and monomeric 42-kDa actin was pooled based upon a previous calibration of the column with rabbit actin. The pool was concentrated by vacuum dialysis against G-buffer (2.5 mM triethanolamine, pH 8.0, 0.5 mM DTT, 0.2 mM ATP, 0.1 mM CaCl$_2$, 0.01% sodium azide), to a volume of 250 μl. Polymerization was initiated by adding ATP to 1 mM, MgCl$_2$ to 4 mM, NaCl to 50 mM, and phalloidin to 25 μM. After an overnight incubation at 0° C., the F-actin sample was dialyzed for 6 hrs against Actin EM Buffer (2 mM Pipes, pH 6.8 at 4° C., 1 mM ATP, 4 mM MgCl$_2$, 50 mM NaCl, 0.5 mM DTT, and 0.02% sodium azide). After dialysis, phalloidin was added to 25 μM, and the F-actin was stored on ice until used for negative stain electron microscopy.

FIG. 4 represents the purification of 42-kDa actin, and also illustrates its binding to DNase I affinity resin. Panel A is a Coomassie stained gel at three stages in the purification. Lane 1 is a sample of the low speed supernatant, which was the fraction absorbed to DNase I affinity resin; lane 2 is a sample of the eluate from the DNase I affinity resin, which was the fraction loaded onto the gel filtration column; lane 3 is a sample of the final 42-kDa actin sample, pooled from the gel filtration column, concentrated and polymerized. Panel B is an immunoblot of fractions from the gel filtration column. Lane 1 is a sample from a fraction in the void volume; lane 2 is a sample from the pool of fractions containing monomeric actin. 29-kDa actin elutes in the void volume of the column, with some co migrating 42-kDa actin. The majority of the 42-kDa actin elutes as a discrete peak of monomers.

3. Purified 42-kDa Actin Binds Myosin S-1 in an ATP Sensitive Manner

The two most characteristic properties of native actin are the ability to polymerize into filaments and the ability to bind myosin. After purification, the actin exhibits both properties. FIG. 5 shows filaments of polymerized actin solubilized by this procedure are able to bind myosin S-1 in an ATP sensitive manner. Since the denaturation of actin is irreversible, these properties indicate that the actin was never denatured by Sarkosyl lysis. Panel A shows actin filaments incubated with myosin S-1 in the presence of ATP. Electron microscope grids were negatively stained with 1% uranyl acetate. The magnification of Panels A and B are the same. The inset shows actin filaments from a sample which was not incubated with myosin. The magnification bar represents 26.7 nm. Panel B shows actin filaments incubated with myosin S-1 in the absence of ATP. Grids were stained as in Panel A. The distance between consecutive myosin S-1 arrowheads is 35.5 nm±0.11 (S.E.). The magnification bar represents 40 nm.

4. 29-kDa Actin Binds DNase I

Most forms of actin bind to DNase I with very high affinity. It was therefore possible to assay a relatively crude bacterial fraction from the actin producing strain using DNase I affinity chromatography.

All procedures for the DNase I Binding Assay were at 4° C. or on ice. The high speed supernatant obtained after Sarkosyl lysis was supplemented with PMSF to 0.5 mM and sodium azide to 0.02%. The following were added to tubes containing DNase I resin or control resin: 10 ml portions of the supernatant and either a DNase I stock solution or stock buffer. The reaction mixtures were gently mixed for 2 h, the resins pelleted, the unbound fractions removed, and the resins resuspended in 4 bed volumes of high salt buffer (25 mM triethanolamine pH 8 at 4° C., 800 mM NaCl, 0.02% sodium azide, 1.0 mM ATP, 1.0 mM GDP, 5 mM NaPP, 0.5 mM DTT, 0.1 mM EDTA, 1.38 mM $MgCl_2$, 0.95 mM $CaCl_2$, 0.5 mM PMSF: the estimated free concentration of each divalent cation was 0.1 mM). The resins were gently mixed with high salt buffer for 30 min., pelleted, and the washes removed. In most experiments the wash was repeated a second time and both high salt washes were added to the initial unbound fraction. One ml of this combined flow-through+high salt wash fraction was ethanol precipitated, and solubilized for gel analysis.

The binding of D.d. actin was measured by adding pure actin to control lysates and manipulating these lysates in the same manner as lysates which contained 29-kDa actin. The binding of 29-kDa and D.d. actin to DNase I was quantified by immunoblots. Table II shows 29-kDa actin s ability to bind DNase I was equivalant to that of D.d. actin. As a control, the binding of both types of actin to mock resin was tested, and none was found to bind. Another control involved binding to affinity resin in the presence of soluble DNase I.

TABLE II

| BINDING OF 29-kDa AND D.d. ACTIN TO DNase I | |
|---|---|
| | PERCENT BINDING* |
| | 29 kDa Actin |
| CONTROL-SEPHAROSE (without covalently attached DNase I) | −1% ± 2% (4)** |
| DNase I-SEPHAROSE | 20% ± 2% (6) |
| DNase I-SEPHAROSE + 0.5 mg of FREE DNase I | 6% ± 2% (2) |
| DNase I SEPHAROSE + 2.0 mg OF FREE DNase I | −1% ± 2% (4) |
| | D.d. ACTIN |
| CONTROL-SEPHAROSE (without covalently attached DNase I) | 3% (1) |
| DNase I-SEPHAROSE | 19% ± 3% (2) |
| DNase I-SEPHAROSE + 0.5 mg of FREE DNase I | N.D.*** |
| DNase I-SEPHAROSE + 2.0 mg OF FREE DNase I | 0% ± 2% (2) |

*Percent of the loaded fraction retained by the column
**Values are presented as the mean ± SE, when n > 2; the number of independent binding reactions is indicated in parentheses
***Not determined A high speed supernatant was obtained as in Table I. Portions of this were batch absorbed to DNase I affinity resin. The resin used in each binding reaction contained 0.6 mg of immobilized DNase I. After separating the unbound fraction, the resin was washed twice with high salt buffer. The washes were combined with the unbound fraction, and the amount of actin present in this fraction was quantitated by immunoblots. The binding of D.d. actin was measured by adding pure actin to control lysates, and manipulating these lysates in the same manner as lysates which contain 29 kDa actin.

EXAMPLE 2

Solubilization of Bacterially Expressed Actin Obtained After French Press Lysis by the Sarkosyl Extraction Method

Culture Growth

Culture growth was performed the same as in Example 1.

French Press Lysis+Sarkosyl Extraction

At this point all procedures were done at 4° C. or on ice. The bacteria were washed with low salt buffer (10 mM triethanolamine, pH 8 at 4° C., 0.5 mM ATP, 0.5 mM DTT, 0.1 mM $CaCl_2$) and resuspended to a final volume of 20 mls of low salt buffer+protease inhibitors (20 ug/ml aprotinin, 10 ug/ml leupeptin, 2.5 ug/ml pepstatin, 2.5 ug/ml chymostatin). Lysis was in the French pressure cell at 1000 $lb/in^2$., running the lysate through twice. The lysate was centrifuged at 116,500×g for 8 min. (the equivalent of 15,000×g for one hour) to collect insoluble protein. Then, Sarkosyl extraction was performed as follows: the supernatant was removed and the pellet resuspended in 10 ml of a divalent cation free extraction buffer (1.5% Sarkosyl, 25 mM triethanolamine, pH 8.0, 4 mM ATP, 0.8 mM dithiothreitol, 1 mM EDTA, 0.02% sodium azide, 20 ug/ml aprotinin, 5 ug/ml leupeptin, 2.5 ug/ml pepstatin, 2.5 ug/ml chymostatin and 0.5 mM o-phenanthroline) with 30 strokes of a Teflon-glass homogenizer. The effective ranges in the extraction buffer are as follows: Sarkosyl 0.5–2%, pH 6.0–9.0, and 0.5–5 mM EDTA. The extraction buffer may contain any other constituents necessary for the stability of the expressed protein. The resuspension was then re-centrifuged at least at the rate performed before Sarkosyl extraction, here at 116500×g for 16 min., to separate the solubilized protein from the insoluble material. 9 ml of the supernatant was immediately added to 58.5 ml of octylglucoside (OG) buffer (to sequester Sarkosyl in micelles of octylglucoside). The final concentrations after dilution were 2.0% octylglucoside, 0.2% Sarkosyl, 25 mM triethanolamine, 0.8M NaCl, 1.0 mM ATP, 0.2 mM dithiothreitol, 0.02% azide, 0.13 mM EDTA, 20 μg/ml aprotinin, 5 μg/ml leupeptin, 2.5 μg/ml pepstatin, 2.5 μg/ml chymostatin, 0.07 mM o-phenanthroline. After this was mixed, divalent cations were added (0.68 mM $CaCl_2$ gave a free concentration of 0.1 mM); high speed centrifugation was then performed.

In general, Sarkosyl may be sequestered by adding nonionic detergent in at least a 5-fold weight excess over the Sarkosyl detergent. This nonionic detergent may be octylglucoside. Sarkosyl sequestration may be followed by the addition of divalent cations to stabilize the protein.

Sequestration may also be followed by one of three methods to remove all detergent. One method, applicable to sequestration using any nonionic detergent, involves binding the protein to a solid resin matrix and washing all of the detergent out of the resin matrix. A second method, applicable only to sequestration using octylglucoside, involves dialysis in which the dialysis membrane has a molecular weight cut-off of at least 30,000 daltons. A third method, applicable only to sequestration using octylglucoside, involves concentration of the sample using a 30,000 dalton cut off membrane followed by dilution of the concentrated sample into a detergent free solution. Another method of removing detergent does not require sequestration. This alternative method involves precipitation of Sarkosyl by adding a several millimolar excess of divalent cation over EDTA and removing the Sarkosyl by centrifugation.

RESULTS

1. Actin is Soluble After French Press Method + Sarkosyl Extraction

After French press lysis, bacterially-expressed actin is insoluble. FIG. 3 represents fractionation of both 29-kDa actin and 42-kDa actin after French press lysis and Sarkosyl extraction. FIG. 3 shows that insoluble actin recovered after French press lysis was solubilized by Sarkosyl extraction. However, the bacterial outer membrane proteins were not solubilized by Sarkosyl extraction, and could be completely separated from the solubilized actin. Panel A is a Coomassie-stained gel. Panel B is an immunoblot of the same samples as in Panel A. Lane 1 is a sample of total lysate; lane 2 is a sample from the low speed pellet; lane 3 is a sample of the Sarkosyl extraction supernatant; lane 4 is a sample from the Sarkosyl extraction pellet.

2. 29-kDa Actin Binds DNase I After Sarkosyl Extraction

The high speed supernatant obtained after Sarkosyl extraction was bound to DNase I affinity resin. The ability of 29-kDa actin to bind was equivalent to that seen in Table II after Sarkosyl lysis.

EXAMPLE 3

Solubilization of Myosin Light Chain Kinase, Obtained After French Press Lysis, by the Sarkosyl Extraction Method

*Dictyostelium discoidium* myosin light chain kinase is not a structural protein, like actin, but is an enzyme which specifically phosphorylates the myosin light chain. When expressed in *E. coli*, the kinase is insoluble, and the aggregates can only be solubilized using strong denaturants such as 8M urea. However, tests performed at Stanford University show that the kinase can be differentially extracted from the aggregates with Sarkosyl detergent (0.5% + 1 mM EDTA), such that virtually all of the kinase is solubilized but bacterial proteins (presumably outer membrane proteins) are not. The extracted kinase is still enzymatically active. Starting from the same quantity of aggregated protein, 10-fold more kinase activity is recovered using Sarkosyl solubilization when compared to urea solubilization. Soluble kinase is also obtained when bacteria are lysed in the presence of Sarkosyl (Sarkosyl lysis), but the kinase obtained by this procedure was not extensively characterized for the retention of enzymatic activity.

The results obtained with the kinase are significant for the following reasons: (1) the protein is significantly different from actin, (2) the protein has an easily quantitated enzymatic activity, (3) the protein is expressed to very high levels in *E. coli*, unlike full length wild type actin, and is therefore more representative of commercial applications of this technology.

We claim:

1. A method of solubilizing bacterially-expressed proteins which comprises lysing of the bacterial host cells, centrifuging to collect insoluble protein, extracting the insoluble protein using a mixture of about 0.5–2.0% Sarkosyl detergent and about 0.5–5 mM EDTA, and re-centrifuging.

2. A method of solubilizing bacterially-expressed proteins which comprises:
   (a) lysing bacteria;
   (b) collecting the insoluble protein by centrifugation to obtain a supernatant and a pellet fraction;
   (c) removing the supernatant and resuspending the pellet fraction in a divalent cation-free extraction buffer consisting of about 0.5–2.0% Sarkosyl detergent, about 0.5–5 mM EDTA, a pH of 8.0, and disulfide reducing reagent; and
   (d) separating solubilized protein from insoluble material by re-centrifugation.

3. A method according to claim 2 wherein the conventional method of lysing is selected from the group consisting of sonication, French press method, and lysozyme digestion followed by freezing and thawing.

4. A method according to claim 3 wherein the French press method comprises pelleting bacteria after growth, resuspending in a solution consisting of no salt, several millimolar buffer at pH 8.0, disulfide reducing reagent and low levels of calcium, lysing in the French pressure cell, and centrifuging the lysate at a speed equivalent to 15000×g for one hour.

5. A method according to claim 2 wherein the divalent cation-free extraction buffer is at any concentration, and at a pH between 6.0 and 9.0.

6. A method according to claim 2 wherein the divalent cation-free extraction buffer is able to contain other constituents necessary for the stability of the expressed protein.

7. A method according to claim 2 wherein the re-centrifugation performed after Sarkosyl extraction is at least equivalent to the centrifugation performed before Sarkosyl extraction.

8. A method according to claims 1 and 2 wherein Sarkosyl is N-lauryl sarcosine or any other detergent which is an N-amide derivative of sarcosinate.

9. A method according to claim 2 which further comprises the step of sequestering or removing the Sarkosyl.

10. A method according to claim 9 wherein Sarkosyl sequestration comprises adding nonionic detergent in at least a 5-fold weight excess over the Sarkosyl detergent.

11. A method according to claim 10 wherein the nonionic detergent is octylglucoside.

12. A method according to claim 9 wherein Sarkosyl sequestration is followed by the addition of divalent cations to stabilize the protein.

13. A method according to claim 9 wherein the Sarkosyl sequestration is followed by binding the protein to a solid resin matrix and washing all detergent out of the resin matrix.

14. A method according to claim 9 wherein Sarkosyl sequestration is followed by dialyzing out the detergent with 30,000 dalton cut-off dialysis membranes.

15. A method according to claim 9 wherein Sarkosyl sequestration is followed by concentrating the solution using a 30,000 dalton cut-off membrane and then diluting the concentrated solution into a detergent-free solution.

16. A method according to claim 2 wherein the final centrifugation is followed by Sarkosyl precipitation, which comprises adding a several millimolar excess of divalent cation over EDTA and removing the Sarkosyl by centrifugation.

* * * * *